(12) United States Patent
Yamada

(10) Patent No.: US 7,914,146 B2
(45) Date of Patent: Mar. 29, 2011

(54) OPHTHALMOLOGICAL PHOTOGRAPHIC APPARATUS

(75) Inventor: Chikako Yamada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/581,777

(22) Filed: Oct. 19, 2009

(65) Prior Publication Data

US 2010/0097575 A1    Apr. 22, 2010

(30) Foreign Application Priority Data

Oct. 20, 2008    (JP) .................................. 2008-269958

(51) Int. Cl.
*A61B 3/14*    (2006.01)
*A61B 3/00*    (2006.01)

(52) U.S. Cl. .................... 351/206; 351/200; 351/246

(58) Field of Classification Search .................. 351/200, 351/205–206, 246
See application file for complete search history.

(56) References Cited

U.S. PATENT DOCUMENTS

| 6,456,787 | B1 | 9/2002 | Matsumoto | |
| 2004/0184000 | A1* | 9/2004 | Hayashi | ........................ 351/222 |
| 2006/0028617 | A1 | 2/2006 | Matsumura | |

FOREIGN PATENT DOCUMENTS

| JP | 11-267104 | 10/1999 |
| JP | 2000-316812 | 11/2000 |
| JP | 2003-230540 | 8/2003 |
| JP | 2003-230540 A | 8/2003 |
| JP | 2006-158864 | 6/2006 |

* cited by examiner

*Primary Examiner* — Ricky L Mack
*Assistant Examiner* — Dawayne A Pinkney
(74) *Attorney, Agent, or Firm* — Canon U.S.A., Inc., IP Division

(57) ABSTRACT

An ophthalmological photographic apparatus includes an observation moving-image photographic unit configured to photograph an observation moving image of a subject's eye, a still-image photographic unit configured to photograph a still image of the subject's eye, an image display unit configured to display at least one of the observation moving image and the still image, and a display content control unit configured to cause the image display unit to display one of the observation moving image and the still image when the still-image photographic unit photographs a still image.

7 Claims, 4 Drawing Sheets

OPHTHALMOLOGICAL PHOTOGRAPHIC APPARATUS

BACKGROUND OF THE INVENTION

1. Field of the Invention

The present invention relates to an ophthalmological photographic apparatus for performing ophthalmological fluorescent photography.

2. Description of the Related Art

Until now, there has been known an ophthalmological photographic apparatus in which a subject is intravenously injected with a fluorescent agent to cause illumination light to excite the fluorescent agent in the vein to perform fluorescent photography on a subject's fundus. The amount of the fluorescent agent flowing into the vein of the fundus suddenly increases at a specific period of time after the fluorescent agent was intravenously injected and then gradually decreases. At an initial fluorescence stage immediately after the fluorescent agent was intravenously injected, the fluorescent agent first flows into a thick blood vessel and then flows into narrower capillary vessels, so that the flowing state of the fluorescent agent (along with the blood of the subject) drastically changes.

In fluorescent photography, it is important to observe this change in detail. Japanese Patent Application Laid-Open No. 2003-230540 discusses a system for continuously photographing a fundus image while allowing an operator to observe the fundus image at the time of the fluorescent photography.

In a later fluorescence stage in which a further period of time has passed after the fluorescent agent was intravenously injected, the fluorescent agent is delivered throughout the veins, so that a flowing state does not change so much. For this reason, in the later fluorescence stage, a change is small in the flowing state, so that continuous photographing is not necessary and observation is not very important either.

Still images to be photographed may be few in number in the later fluorescence stage, thus allowing an immediate determination of whether the photography is successful and a resulting efficient balance between a manageable number of photographs and obtaining the required information in the photographs.

However, it is difficult to determine whether the current stage is the initial fluorescence stage or later fluorescence stage at the time of photographing a still image, so that the fluorescent photography cannot be smoothly timed.

SUMMARY OF THE INVENTION

The present invention is directed to an ophthalmological photographic apparatus capable of efficiently performing photography by switching the contents displayed on an image display unit depending on the fluorescence stages of a fluorescent agent injected in the person being photographed.

According to an aspect of the present invention, an ophthalmological photographic apparatus includes an observation moving-image photographic unit configured to photograph an observation moving image of a subject's eye, a still-image photographic unit configured to photograph a still image of the subject's eye, an image display unit configured to display at least one of the observation moving image and the still image, and a display content control unit configured to cause the image display unit to display one of the observation moving image and the still image when the still-image photographic unit photographs a still image.

According to another aspect of the present invention, an ophthalmological photographic apparatus includes an observation moving-image photographic unit configured to photograph an observation moving image of a subject's eye, a still-image photographic unit configured to photograph a still image of the subject's eye, a fluorescence stage determination unit configured to determine whether an intravenously injected fluorescent agent is in an initial fluorescence stage or a later fluorescence stage, an image display unit configured to display both the observation moving image and the still image, and a display content control unit configured to cause the image display unit to display the observation moving image made larger than the still image both at the initial fluorescence stage and at the later fluorescence stage at the time of observation of a moving image, to display the observation moving image made larger than the still image at the initial fluorescence stage at the time of photographing of a still image by the still-image photographic unit, and to display the still image made larger than the observation moving image at the later fluorescence stage at the time of photographing of a still image by the still-image photographic unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate non-limitative exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
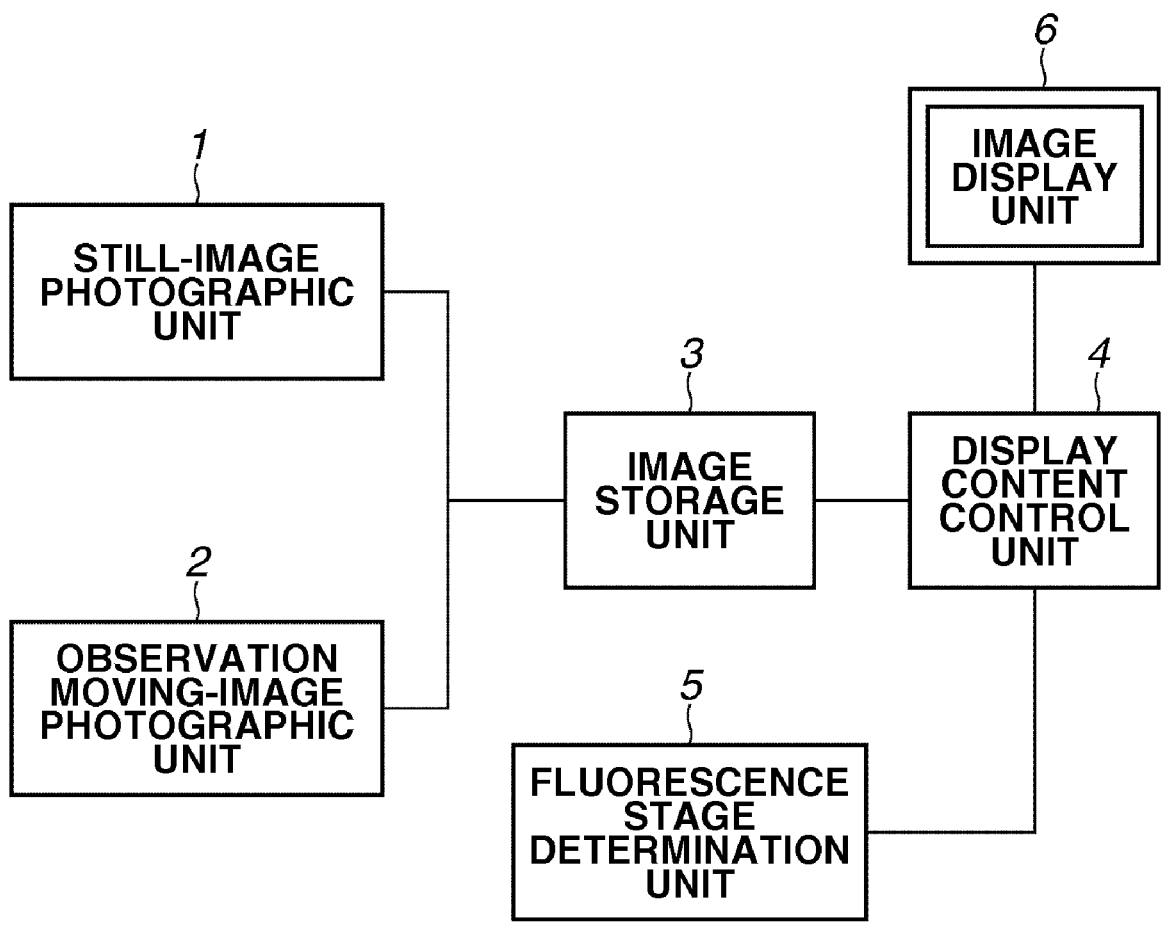
FIG. 1 is a block diagram illustrating a configuration of an ophthalmological photographic apparatus according to an exemplary embodiment of the present invention.

FIG. 1 is a block diagram illustrating a configuration of an ophthalmological photographic apparatus according to a first exemplary embodiment of the present invention. The outputs of a still-image photographic unit 1 and an observation moving-image photographic unit 2 are connected to a display content control unit 4 via an image storage unit 3. A fluorescence stage determination unit 5 and an image display unit 6 are connected to the display content control unit 4.

Both a still image of a subject's eye photographed by the still-image photographic unit 1 and an observation moving image of the subject's eye photographed by the observation moving-image photographic unit 2 are stored in the image storage unit 3. By "observation" moving image, it is understood that the moving image may be observed by an operator in real-time. Alternatively or additionally, the moving-image data may be stored and observed with a delay or at a later date. The display content control unit 4 acquires the observation moving image or the still image from the image storage unit 3 to display it on the image display unit 6 and determines whether the current fluorescence stage is the initial fluorescence stage or later fluorescence stage via the fluorescence stage determination unit 5.

Figure 2:
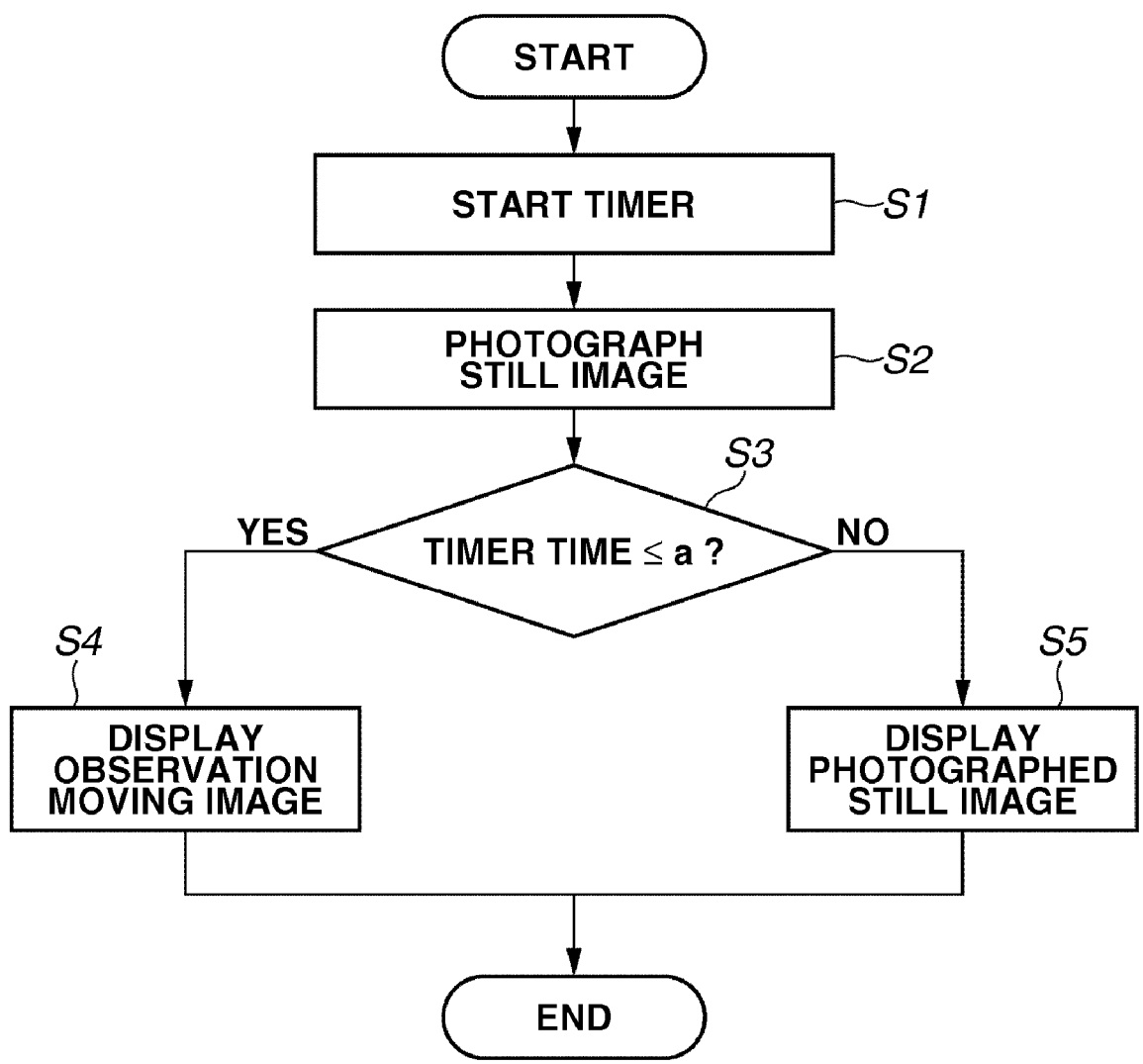
FIG. 2 is a flow chart illustrating fluorescent photography according to an exemplary embodiment of the present invention.

FIG. 2 is a flow chart illustrating fluorescent photography according to the first exemplary embodiment. At first, a fluorescent photographic mode is selected by an operator switching a photographic mode-changing switch (not shown) to start the fluorescent photography. In step S1, a timer incorporated in the fluorescence stage determination unit 5 starts timing. The timing may be started by the operator pressing a timer start switch (not shown) or automatically started at an arbitrary or predetermined timing.

The operator observes a change in the fluorescent agent while observing the observation moving image of a subject's fundus displayed on the image display unit 6 and also adjusts alignment for photographing a still image. After the alignment has been finished, then in step S2, the operator operates a switch (not shown) to photograph a still image, so that the still image data obtained by the still image photographic unit 1 is stored in the image storage unit 3. The image storage unit 3 may be a volatile or a nonvolatile storage device.

Since a change in a state where the fluorescent agent flows into the blood vessels is drastic at the initial fluorescence stage immediately after the fluorescent agent is intravenously injected, the operator needs to photograph a large number of still images within a short time while observing a change in the fluorescent agent.

In step S3, the timer incorporated in the fluorescence stage determination unit 5 indicates whether a predetermined time "a" has elapsed. For example, if the predetermined time "a" is set to 10 minutes, the fluorescence stage determination unit 5 determines, using its timer, that the fluorescence stage has changed to the later fluorescence stage after 10 minutes have elapsed. If the predetermined time "a" has not yet elapsed (i.e. the present time is less than "a," depicted as YES in step S3), the process proceeds to step S4. In step S4, the display content control unit 4 displays an observation moving image on the image display unit 6. If the predetermined time "a" has elapsed (i.e. the present time is greater than "a," depicted as NO in step S3), the process proceeds to step S5. In step S5, the display content control unit 4 displays a still image on the image display unit 6.

Figure 3:
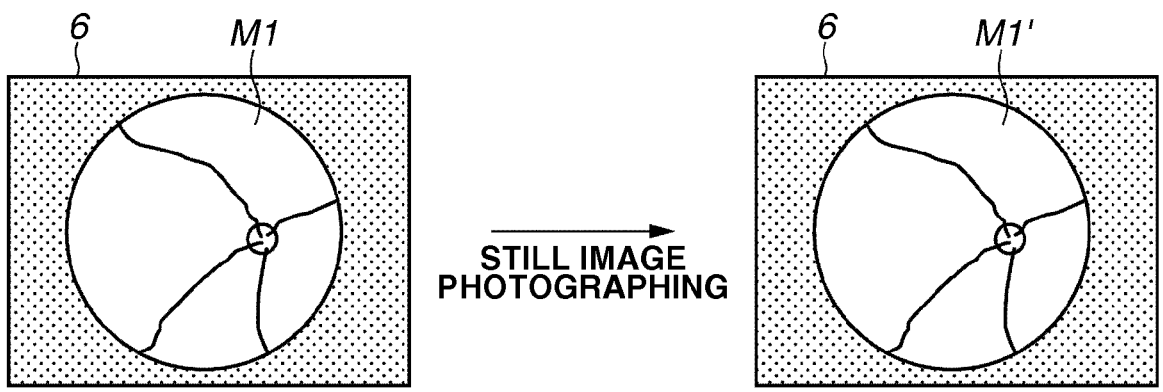
FIG. 3 is a chart illustrating a method for controlling the display at the initial fluorescence stage according to a first exemplary embodiment of the present invention.

FIG. 3 is a chart illustrating a method for controlling the image display unit 6 at the initial fluorescence stage according to the first exemplary embodiment. When the fluorescent photography is started, the observation moving-image data photographed by the observation moving-image photographic unit 2 is stored in the image storage unit 3. The display content control unit 4 acquires the observation moving-image data from the image storage unit 3 to display an observation moving image M1 on the image display unit 6.

If the operator photographs a still image during the initial fluorescence stage determined, the still-image data photographed by the still-image photographic unit 1 is stored in the image storage unit 3. The display content control unit 4 continues to acquire the observation moving-image data photographed by the observation moving-image photographic unit 2 from the image storage unit 3 to display an observation moving image M1' on the image display unit 6.

This enables the operator to continue to observe a state where the fluorescent agent flows using the observation moving image M1' even immediately after the still image was photographed and to concentrate on the operation of photographing the following still image, thus allowing continuous photography over a short time.

Figure 4:
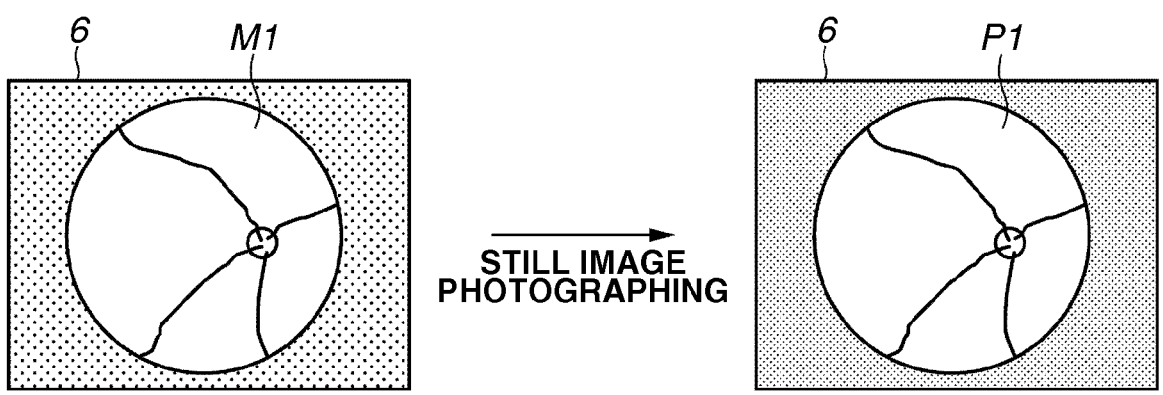
FIG. 4 is a chart illustrating a method for controlling the display at the later fluorescence stage according to the first exemplary embodiment.

FIG. 4 is a chart illustrating a method for controlling the image display unit 6 at the later fluorescence stage according to the first exemplary embodiment. The observation moving-image data photographed by the observation moving-image photographic unit 2 is stored in the image storage unit 3 before the still-image is photographed and the display content control unit 4 acquires the observation moving-image data from the image storage unit 3 to display the observation moving image M1 on the image display unit 6.

A change in a state where the fluorescent agent flows is small at the later fluorescence stage during which the fluorescent agent is delivered throughout the veins, so that the operator does not need to continue with the continuous photography. Specifically, the operator may take photographs at an interval of 5 to 10 minutes, for example.

The operator may photograph a still image while the fluorescence stage determination unit 5 determines that the fluorescence stage has changed to the later fluorescence stage. In this case, the display content control unit 4 acquires the observation still image photographed by the still-image photographic unit 1 from the image storage unit 3 to display a still image P1 on the image display unit 6. This enables the operator to confirm the still image P1 immediately after photographing to instantly determine whether re-photographing is needed.

Figure 5:
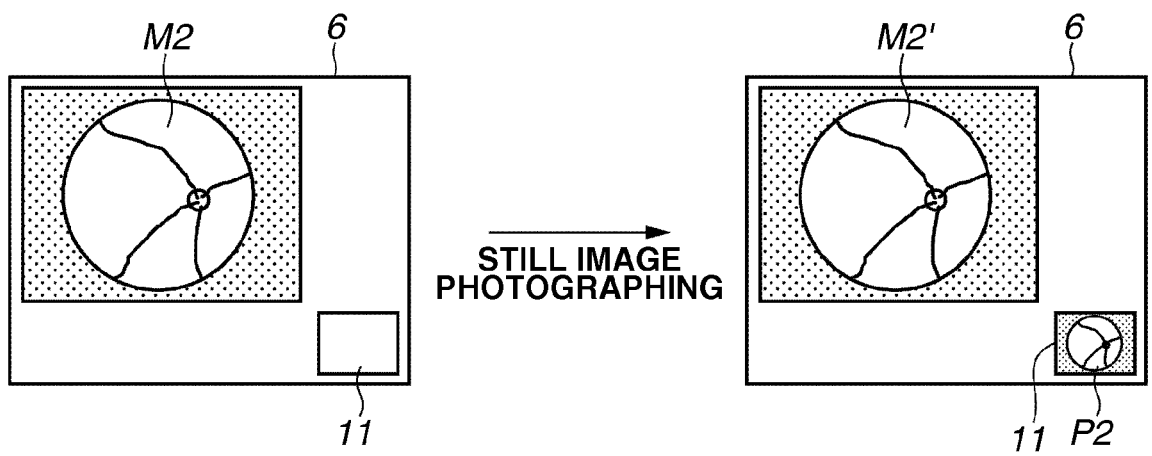
FIG. 5 is a chart illustrating a method for controlling the display at the initial fluorescence stage according to a second exemplary embodiment of the present invention.

FIG. 5 is a chart illustrating a method for controlling the image display unit 6 at the initial fluorescence stage according to a second exemplary embodiment of the present invention. When the fluorescent photography is started, the observation moving-image data photographed by the observation moving-image photographic unit 2 is stored in the image storage unit 3. The display content control unit 4 acquires the observation moving-image data from the image storage unit 3 to display an observation moving image M2 in a large display window on the image display unit 6. If no single still image is photographed, an empty display frame or window 11 smaller than the observation moving image M2 is displayed on the lower right corner of the image display unit 6. The operator observes a change in the fluorescent agent while observing the observation moving image M2 of the subject's fundus and also adjusts alignment for photographing a still image at the time of observing the moving image to perform the operation for photographing the still image.

When the operator photographs a still image at the initial fluorescence stage, the display content control unit 4 acquires both the observation moving-image data photographed by the observation moving-image photographic unit 2 and the still-image data photographed by the still-image photographic unit 1 from the image storage unit 3 to display both an observation moving image M2' and a still image P2 on the image display unit 6. At this point, displaying the observation moving image M2' made larger than the still image P2 allows the operator to concentrate on the observation and the photographing of the fundus image at the initial fluorescence stage and to simply confirm the photographed image at the same time.

Figure 6:
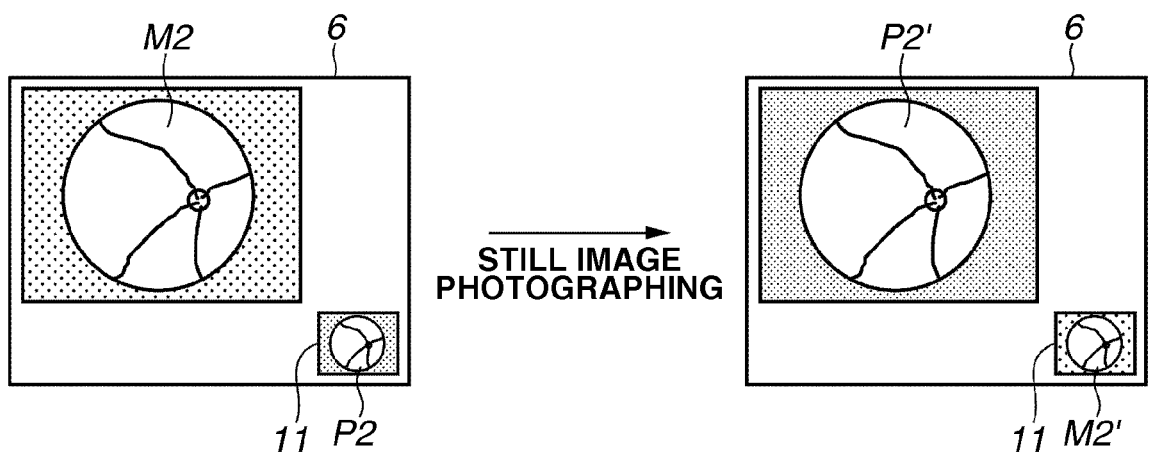
FIG. 6 is a chart illustrating a method for controlling the display at the later fluorescence stage according to the second exemplary embodiment.

FIG. 6 is a chart illustrating a method for controlling the image display unit 6 at the later fluorescence stage according to the second exemplary embodiment. The observation moving-image data photographed by the observation moving-image photographic unit 2 before the still image is photographed is stored in the image storage unit 3. The display content control unit 4 acquires both the observation moving-image data and the latest (or most recently photographed) still-image data photographed by the still-image photographic unit 1 from the image storage unit 3 to display the observation moving image M2 made larger than the still image P2 on the image display unit 6.

When the operator photographs a still image at the later fluorescence stage, the display content control unit 4 acquires both the observation moving-image data photographed by the observation moving-image photographic unit 2 and the still-image data photographed by the still-image photographic unit 1 from the image storage unit 3 to display both the observation moving image M2' and a still image P2' on the image display unit 6. At this point, displaying the still image P2' in a larger display window than the observation moving image M2' (which is displayed on the smaller display window 11) allows the operator to confirm a still image immediately after photographing and to continue a simple observation at the same time.

In the first and second exemplary embodiments described above, the timer is incorporated in the fluorescence stage determination unit 5, and based on the output of the timer, it is determined whether the initial fluorescence stage has changed to the later fluorescence stage. However, it may be determined whether the initial fluorescence stage has changed to the later fluorescence stage by using an optical sensor (not shown) for detecting that the amount of fluorescent light from the subject's fundus is less than a predetermined reference value.

The above exemplary embodiments are described using the still-image photographic unit and the observation moving-image photographic unit, which are different from each other. However, observation and photograph may be performed by a single photographic apparatus.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-269958 filed Oct. 20, 2008, which is hereby incorporated by reference herein in its entirety.

What is claimed is:

1. An ophthalmological photographic apparatus comprising:
    an observation moving-image photographic unit configured to photograph an observation moving image of a subject's eye;
    a still-image photographic unit configured to photograph a still image of the subject's eye;
    a determination unit configured to determine that a fluorescence stage of the subject's eye has shifted from an initial fluorescence stage to a later fluorescence stage; and
    a display control unit configured to cause an image display unit to prioritize displaying the still image over the moving image, when the determination unit determines that the fluorescence stage of the subject's eye is the later fluorescence stage and when the still image is photographed while the moving image being photographed is displayed.

2. The ophthalmological photographic apparatus according to claim 1,
    wherein the display control unit causes the display unit to continue to display the moving image, when the determination unit determines that the fluorescence stage of the subject's eye is the initial fluorescence stage and when the still image is photographed while the moving image being photographed is displayed.

3. The ophthalmological photographic apparatus according to claim 1, wherein the determination unit is either a timer or a sensor for detecting a fluorescence amount.

4. The ophthalmological photographic apparatus according to claim 1, further comprising:
    a re-photographing determination unit configured to determine whether the still image needs to be re-photographed or not in accordance with a photographic state of the still image.

5. An ophthalmological photographic apparatus comprising:
    an observation moving-image photographic unit configured to photograph an observation moving image of a subject's eye;
    a still-image photographic unit configured to photograph a still image of the subject's eye;
    a fluorescence stage determination unit configured to determine that a fluorescence stage of the subject's eye has shifted from an initial fluorescence stage to a later fluorescence stage; and
    a display content control unit configured to cause an image display unit to display the observation moving image made larger than the still image both at the initial fluorescence stage and at the later fluorescence stage at the time of observation of a moving image, to display the observation moving image made larger than the still image at the initial fluorescence stage at the time of photographing of a still image by the still-image photographic unit, and to display the still image made larger than the observation moving image at the later fluorescence stage at the time of photographing of a still image by the still-image photographic unit.

6. An ophthalmological photographic method comprising the steps of:
    photographing a moving image of a subject's eye;
    photographing a still image of the subject's eye;
    determining that a fluorescence stage of the subject's eye has shifted from an initial fluorescence stage to a later fluorescence stage; and
    prioritizing displaying the still image over the moving image when it is determined that the fluorescence stage is the later fluorescence stage and when the still image is photographed while the moving image being photographed is displayed.

7. The ophthalmological photographic method of claim 6, further comprising the step of:
    continuing to display the moving image when it is determined that the fluorescence stage is the initial fluorescence stage and when the still image is photographed while the moving image being photographed is displayed.

* * * * *